(12) United States Patent
Smith-Reynolds

(10) Patent No.: US 9,408,992 B2
(45) Date of Patent: Aug. 9, 2016

(54) METHOD AND APPARATUS FOR REVERSIBLY CONNECTING A NASAL TUBE TO A PERSON'S CLOTHING

(71) Applicant: Moniqua Smith-Reynolds, Lakewood, CO (US)

(72) Inventor: Moniqua Smith-Reynolds, Lakewood, CO (US)

(*) Notice: Subject to any disclaimer, the term of this patent is extended or adjusted under 35 U.S.C. 154(b) by 0 days.

(21) Appl. No.: 14/566,285

(22) Filed: Dec. 10, 2014

(65) Prior Publication Data

US 2015/0165153 A1 Jun. 18, 2015

Related U.S. Application Data

(60) Provisional application No. 61/914,516, filed on Dec. 11, 2013, provisional application No. 62/046,432, filed on Sep. 5, 2014.

(51) Int. Cl.
*A61M 16/06* (2006.01)

(52) U.S. Cl.
CPC ....... *A61M 16/0683* (2013.01); *A61M 16/0666* (2013.01); *A61M 2205/0272* (2013.01); *A61M 2209/088* (2013.01); *Y10T 24/13* (2015.01); *Y10T 24/32* (2015.01)

(58) Field of Classification Search
CPC . Y10T 24/32; Y10T 24/13; A61M 2025/024; A61M 2209/088; A61M 16/0683; A61M 16/0666
USPC .......................................................... 24/303
See application file for complete search history.

(56) References Cited

U.S. PATENT DOCUMENTS

| | | | |
|---|---|---|---|
| 2,592,395 A * | 4/1952 | Cummings | A44B 6/00 24/303 |
| 4,336,806 A * | 6/1982 | Eldridge, Jr. | A61M 25/02 128/DIG. 26 |
| 4,447,238 A * | 5/1984 | Eldridge, Jr. | A61M 25/02 128/DIG. 26 |
| 5,400,776 A * | 3/1995 | Bartholomew | A61M 25/02 128/200.24 |
| 5,682,653 A * | 11/1997 | Berglof | G09F 1/10 224/183 |
| 6,367,126 B1 | 4/2002 | Rivkin | |
| 6,568,805 B1 | 5/2003 | Dietz | |
| 6,622,349 B2 | 9/2003 | Wong | |
| 6,623,349 B2 | 9/2003 | Fletcher | |
| 6,848,783 B2 | 2/2005 | Dietz | |
| 6,848,787 B2 | 2/2005 | Dietz | |
| 7,114,806 B2 | 10/2006 | Dietz | |
| 7,185,982 B2 | 3/2007 | Dietz | |
| 7,207,091 B2 | 4/2007 | Dunaye | |
| 7,296,889 B2 | 11/2007 | Dietz | |
| 7,494,217 B2 | 2/2009 | Jongebloed, Jr. | |
| 7,496,991 B2 | 3/2009 | Avery | |
| 7,721,392 B2 | 5/2010 | Avery | |
| 7,793,518 B1 * | 9/2010 | Holleman | A41F 19/00 2/1 |
| 7,892,110 B2 | 2/2011 | Bertolino, Jr. | |
| 7,992,264 B2 | 8/2011 | Abadi | |

(Continued)

FOREIGN PATENT DOCUMENTS

WO    WO 2007/103650    9/2007

*Primary Examiner* — Abigail Morrell
(74) *Attorney, Agent, or Firm* — Sheridan Ross P.C.

(57) ABSTRACT

A nasal tube fastener for securing a nasal tube to a person's clothing so as to reduce the opportunity for the tube to be entangled with other objects or to get in the way of the wearer of the tube, such fastener comprising a pair of engageable magnetic fasteners of opposite polarity to each other, the magnetic portions preferably connected to each end of a strap engagement portion connected to each magnetic fastener and extending transverse thereto.

1 Claim, 9 Drawing Sheets

(56) References Cited

U.S. PATENT DOCUMENTS

| | | |
|---|---|---|
| 8,235,262 B1 | 8/2012 | Sakdol |
| 8,469,511 B2 | 6/2013 | Miller et al. |
| 8,615,853 B2 | 12/2013 | Rathbun |
| 8,696,112 B1 | 4/2014 | Vaught |
| 2008/0104742 A1* | 5/2008 | Alperin .................. A41F 17/02 2/321 |
| 2010/0083699 A1* | 4/2010 | Conigliaro ........... A44C 15/003 63/1.18 |
| 2010/0312127 A1 | 12/2010 | Fumuro et al. |
| 2012/0118923 A1 | 5/2012 | Allen |

* cited by examiner

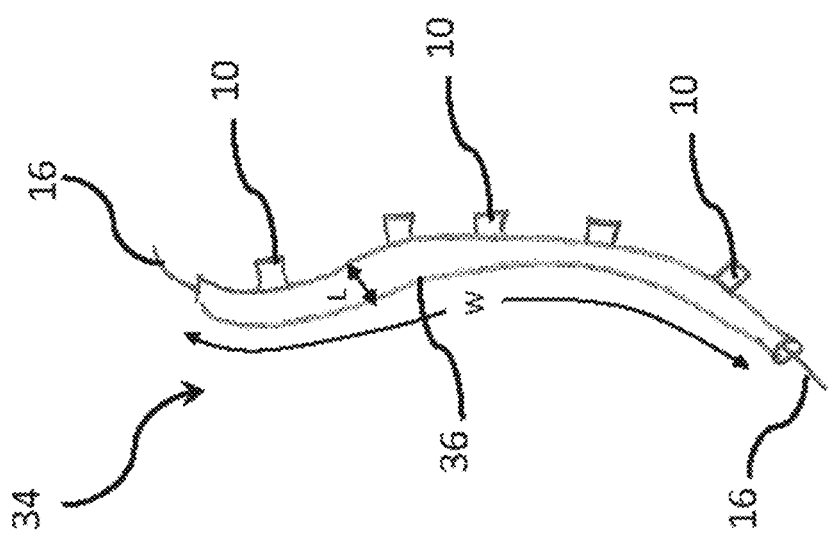

METHOD AND APPARATUS FOR REVERSIBLY CONNECTING A NASAL TUBE TO A PERSON'S CLOTHING

CROSS REFERENCE TO RELATED APPLICATIONS

This application claims priority under 35 U.S.C. §119(e) to U.S. Provisional Patent Application Ser. No. 61/914,516 filed Dec. 11, 2013 and 62/046,432 filed Sep. 5, 2014, which are incorporated herein in their entirety by reference.

TECHNICAL FIELD

This invention pertains generally to magnetic clasps for nasal tubes that descend from a person wearing an oxygen dispensing device, and more particularly to an improved magnetic clasp developed for maintaining tubes out of the way of a person, preferably reversibly connected to the clothing of a person, so as to avoid tripping on or entanglement of the tubes.

BACKGROUND OF INVENTION

Existing clasps for nasal tubes mainly consists of simple clothespin devices that are clunky and uncomfortable and present an undesired cosmetic component that individuals wearing nasal tubes do not desire. Such clasps are bulky and large in comparison to the tubes that they contact and are generally unattractive. Some such clasps are such that they are too difficult for a person to manipulate easily, leading to their misuse or non-use. Others are such that they may not release from their secured position in the event of significant force being applied. Thus, while securement of a nasal tube out of the way and away from danger is desired, there exists a need for a simple, inexpensive, attractive, method and device for securing a nasal tube to a person's clothing in a reversible fashion that does not unduly wrinkle or threaten to tear such clothing when a significant force is applied to the nasal tube associated therewith.

SUMMARY OF THE INVENTION

The problems involved in wearing nasal tubes when touting about oxygen tanks are many, including but not limited to having the dangling tubes being caught up with separate objects when moving around, having pets get tangled in such tubing and various other undesired tugging or pulling of the tubes. When grandchildren attempt to give a warm hug to a grandparent that has such tubes in place, the tubes can be pulled and cause pain or injury to the person wearing the nasal tubes, thus potentially limiting such family embraces and putting a damper on normal human relations so needed and desired by those hooked up with oxygen. While at times this is a mere nuisance, at other times, it represents a true danger of having the nasal tubes forcefully removed from a person's face, thus leading to bleeding, pain and other discomfort, including the need to reestablish oxygen supply in a prompt fashion. Such traumatic events often involve screaming at a pet and frustration by health care assistants and family members, and also leads to future trepidation in moving, which causes advanced problems when mobility is often required for physical therapy and practical reason. Oxygen tank burdened individuals with nasal tubes dangling in front or alongside the person thus create the potential for fearful events to transpire, causing unnecessary worry by such individuals. Worse yet, actual unintended contact between the dangling nasal tubes and other items, pets or persons has caused pain and injuries. Thus, this is a long felt but unsolved need that has not been adequately addressed in the prior art.

One aspect of the present invention is directed to the use of a magnetic clasp for such medical tubing, primarily nasal tubes, permitting the user to engage and disengage the clasp without difficulty or significant fine motor manipulation. Such a device would permit reversible attachment of nasal tubes to a person's clothing or wardrobe without damaging such clothing or adversely pinching the nasal tubes. Preferably the conformation of the device is such that it cradles the nasal tube in a manner that secures the tube in a physical position that is away from the threat of being entangled as mentioned above. In the event such unintended snagging of the nasal tube does occur, the device would initially be secured enough to the clothing such that the clothing would take up the stress and forces involved, thus alerting the person to the situation, prior to the nasal tube being forcefully yanked from the person's nostrils. Even when the force is great enough to not only cause the clothing associated with the device and the tube to be pulled, but such force is enough to cause the device to be dissociated with the clothing, at least the device acts as a dampening agent so as to spare the full effect of such a pulling force on the delicate nostril tissues at the end of the tube. This aspect of the present invention is believed to be distinct from other prior art clips where the contact with clothing may be so string that the clothing would tear if excessive force is exerted on a nasal tube. Thus, while the various preferred devices of the present invention permit secure attachment of a nasal tube to one's clothing, such attachment is not so secure as to permit tearing or ripping of the clothing in the event of a forceful pulling event on the nasal tube. One can select and adjust for such contact strength characteristics via the selection of the type, number and placement of magnets to employ under the particular situations involved. Examples of some magnetic securing devices may be found in U.S. Pat. Nos. 6,367,126; 6,623,349; 7,207,091; 6,568,805; 6,848,783; 6,848,787; 7,114,806; 7,185,982; 7,296,889; 7,494,217; 7,496,991; 7,721,392; 7,892,110; 7,992,264; 8,235,262; 8,469,511; 8,615,853; 8,696,112; U.S. Patent Publication No. 2010/0312127; and WIPO Publication No. WO 2007/103650; the disclosures of which are incorporated herein by reference in their entirety.

In certain embodiments, the magnetic clasps use quality magnets and are designed to be pulled apart by applying opposing force and are preferably such that they are not too easily disengaged, thus avoiding unintentional or accidental disengagement. Preferably they are designed so that they can be engaged or disengaged with one hand but can resist accidental disengagement.

In one embodiment, the magnetic clasp of the present invention consists of top and bottom sections, each section having a magnet associated therewith. Preferably, the magnetic attracting surfaces consist of mating, fabric covered sections that are pliable, flexible and washable, so that a person can wear them with their clothing in a rather inconspicuous manner. While preferably the magnets employed are of about the same size and strength, although in various embodiments, one magnet may be longer than the other to provide structural resistance to separation at desired sections of the clasp.

In a preferred embodiment the clasps use neodymium magnets—the strongest magnets available. In still further embodiments of the present invention, the clasps may comprise at least one of Alnico, Bismanol, Fernico, Ferrites, and any other suitable magnetic material.

The invention is easy to put on, easy to take off and fastens securely. In so far as most clasps are difficult to remove needing two hands and fine motor manipulation, the present invention can be unlocked with a simple manual manipulation. This maneuver can be done with one hand.

Thus, various embodiments of the invention are directed to a clasp for securing two ends of an elongated item, the clasp comprises a first clasp magnet end and a second clasp member end, the second clasp member having either a second magnet or a metallic attractant metal member, the second clasp member, the second clasp member being configured to be magnetically attracted to the first magnet. Preferably the first and second clasp members have mating profiles that are reversibly separable from each other.

A further aspect of certain embodiments include sections that are comprised of fabric or plastic or non metallic material in-between the claps ends.

A still further aspect of the invention is where at least one of the magnets comprises a neodymium magnet.

Another aspect of the invention is where the first and second magnets are coated with a precious metal.

In certain embodiments of the invention, the device additionally has important information encoded thereon to advise medical personal as to what illness, physical ailments, medication, directives, etc. the person may have—and thus, facilitate communication of such information to medical personal that arrive upon a potentially unconscious or unresponsive person wearing the nasal tube holding device. For example, the device can include information or symbols to reflect a DNR request; a medication or allergy alert; insulin dependent diabetes; etc. (e.g. thus providing warnings as to what medications to potentially administer and which ones should not be so administered).

In one embodiment, a nasal tube fastener includes at least one magnetic member that has a first magnetic surface of a first magnetic polarity and a second magnetic surface selected from the group of a magnetically attractive metal surface and a component that has an opposite magnetic polarity to the first magnetic polarity. The fastener includes a strap (e.g. a length of material, more preferably cloth having sewn in portions that retain the first and second magnetic surfaces at each end of the strap) that extends at least two inches from between the first and second magnetic surfaces and that is adapted to be conformed around a nasal tube, with said first magnetic surface being positioned on one side of a fabric worn by a person fitted with the nasal tube, and with said second magnetic surface positioned on an opposite side of said fabric, whereby a nasal tube is secured to the fabric upon the magnetic attraction of said first and second surfaces to each other, with the fabric therebetween.

Still other embodiments employ more than one separate magnetically attractive clasp device to secure selected sections of the nasal tube extent along a person's front-most portion of a garment, such as a shirt. Thus, one such clasp can be employed toward the neck region of a person whereas another such device can be employed toward the belly-button region of a person, thus securing the nasal tube at two (or more) locations on a person's clothing.

Another embodiment is a nasal tube fastener comprising a loop having a first end and a second end; a first quick-disconnect means associated with the first end of the loop, the first quick-disconnect means having a first magnetic polarity; a second quick-disconnect means associated with the second end of the loop, the second quick-disconnect means having a second magnetic polarity; wherein the first magnetic polarity and the second magnetic polarity have opposing magnetic polarities, and wherein the first quick-disconnect means contacts the second quick-connect means to form an aperture.

Further aspects of the invention will be brought out in the following portions of the specification, wherein the detailed description is for the purpose of fully disclosing preferred embodiments of the invention without placing limitations thereon. One will appreciate that this summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

BRIEF DESCRIPTION OF DRAWINGS

The invention will be more fully understood by reference to the following drawings which are for illustrative purposes only:

FIG. 4 illustrates a further embodiment of the present invention.

REFERENCE NUMERALS

| # | component |
|---|---|
| 10 | Clasp |
| 12 | Cannula |
| 16 | Tubing |
| 18 | First piece of quick-disconnecting means |
| 20 | Second piece of quick-disconnecting means |
| 22 | Loop |
| 24 | Attachment means |
| 26 | Annular space |
| 28 | First interlocking surface |
| 30 | Second interlocking surface |
| 32 | Hole |
| 34 | Retaining device |
| 36 | Tube |
| 38 | Holder |
| 40 | Backing portion |
| 42 | Prong |

DETAILED DESCRIPTION OF EMBODIMENTS

Referring more specifically to the drawings, for illustrative purposes the present invention is embodied in the apparatus generally shown in FIG. 1 through FIG. 5. It will be appreciated that the apparatus may vary as to configuration and as to details of the parts, and that the method may vary as to the specific steps and sequence, without departing from the basic concepts as disclosed herein.

Figure 1:
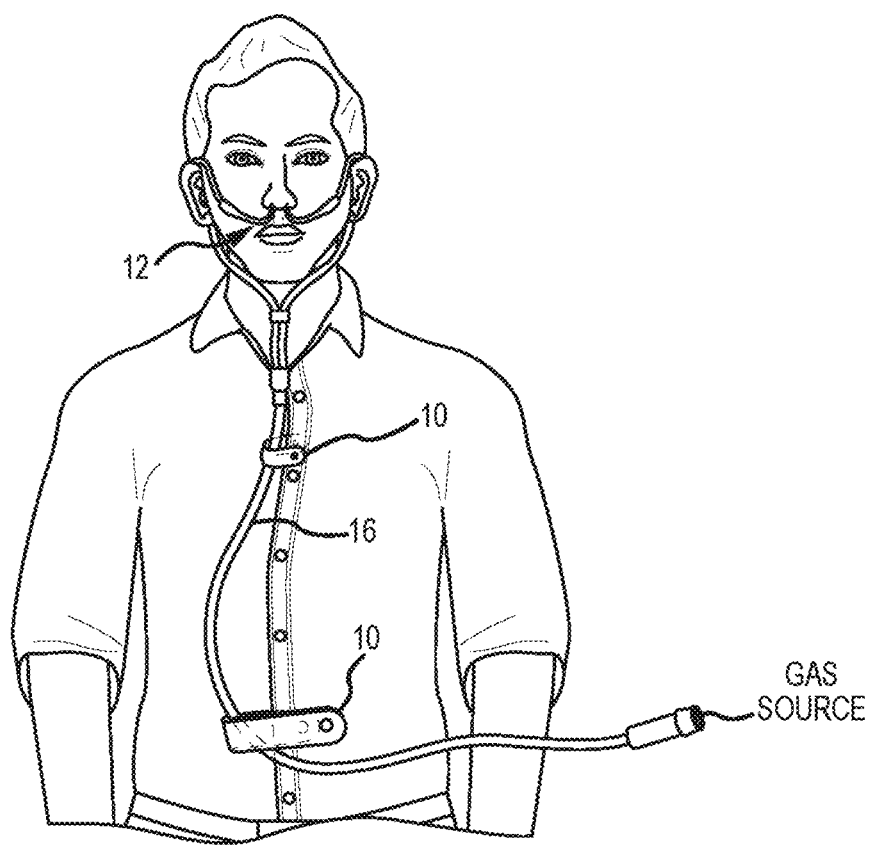
FIG. 1 illustrates the one embodiment of a device having magnetic member attracted to an opposite extent of the device, adapted to retain tubing in reversibly connected association with a wearer's clothing.
Figure 2:
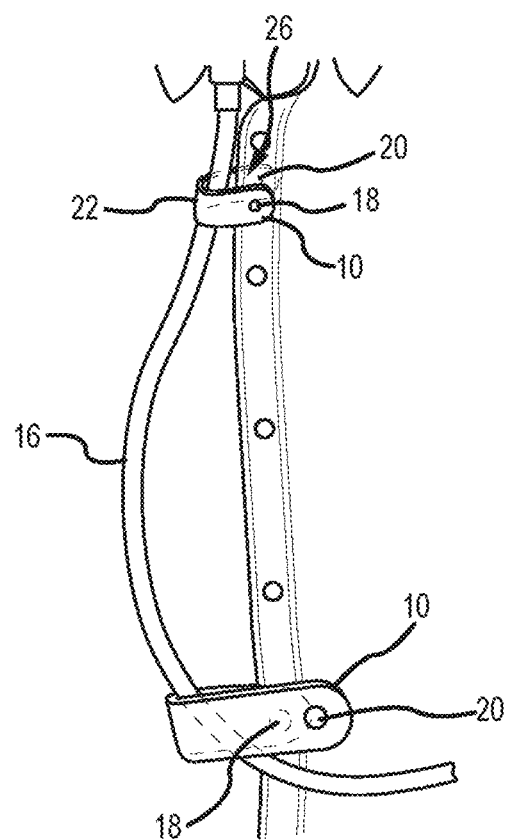
FIG. 2 shows a close-up view of the embodiment illustrated in FIG. 1.

FIGS. 1 and 2 illustrate an exploded perspective view of a fastener 10 in accordance with the present invention. Fastener 10 generally comprises a first quick disconnecting means 18 and a second quick disconnecting means 20 of a material with either opposite or no magnetic properties. In one specific embodiment of the present invention the first quick disconnecting means 18 and the second quick disconnecting means 20 may comprise magnets with opposing polarity such that the provide an attractive force of the aligned magnets (or the one magnet and the opposing metal) that hold the two quick disconnecting means (18 and 20) together.

Figure 3B:
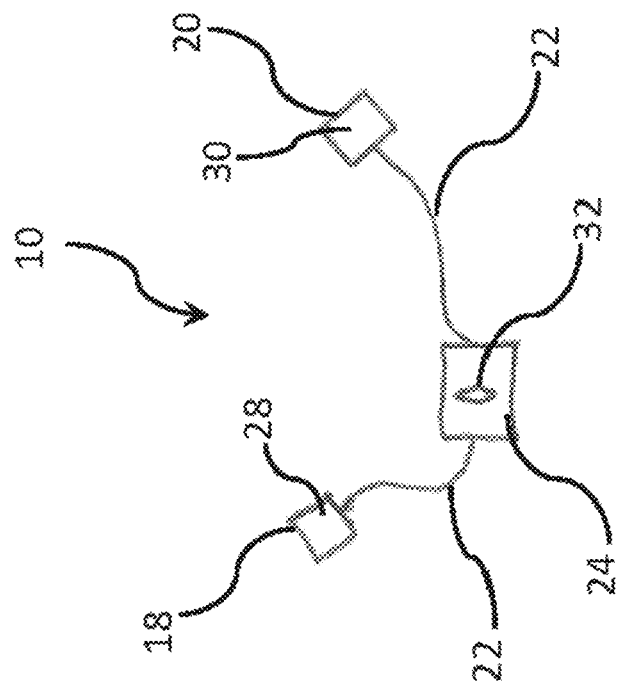
FIG. 3B illustrates another embodiment of the present invention.
Figure 3A:
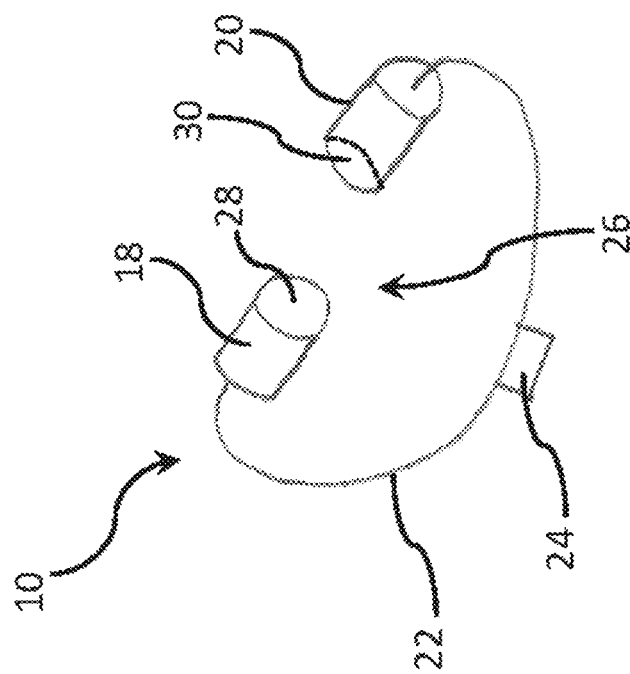
FIG. 3A shows a view of one embodiment of the present invention.

Referring to FIG. 3A, in one embodiment of the present invention, the first quick disconnecting means 18 and the second quick disconnecting means 20 may comprise magnets with interlocking surfaces 28, 30 which may interlock when the magnets (18 and 20) are aligned and mated.

Referring again to FIG. 3A, in a preferred embodiment, when mated, the magnets 18 and 20, provide structural resistance to horizontal separation of interlocking surfaces 28, 30 when opposing force is exerted. In another embodiment of the invention, iron, steel or an iron alloy that is attracted magnetically to the other magnet is substituted for either first or second magnet 18 and 20.

Referring to FIGS. 1, 2, 3A, and 3B, in a preferred embodiment, the first quick disconnecting means 18 and the second quick disconnecting means 20, comprising magnets, utilize magnets made from neodymium and exhibit a strong magnetic flux up to about 15,000 Gauss. A typical grade neodymium magnet may be rated at about 35 grade. In the present invention, about a 48 grade up to about a 60 grade magnet is preferred. In an exemplary embodiment, the neodymium magnets are plated with gold or silver to prevent corrosion and to help shield the magnetic flux emanating from the magnets. Precious metals and/or noble metals such as gold and silver are preferred as a coating because they do not typically cause an allergic reaction when exposed to the skin. Other common coatings, such as nickel, can cause an allergic reaction or skin rash. Neodymium alloy, left uncoated, is subject to corrosion.

In some embodiments of the present invention, the first quick disconnecting means 18 and the second quick disconnecting means 20 may comprise for example, top and bottom sections, or other non-connecting means made of a material or materials without magnetic properties that can absorb or shield the magnetic flux from the magnets. In one embodiment, shielding sections (e.g. top and bottom sections) are made of sterling silver. In a further variation, the sterling silver is plated with 22 k or 24 k gold. In another embodiment, top, bottom sections 22, 24 are made of bronze. In one variation, the bronze is plated with 22 k or 24 k gold. In another variation, the bronze has a 200 mill silver plate. Precious metals are preferred as a coating because they do not typically cause an allergic reaction when exposed to the skin. The non-magnetic magnetic portions of the clasp, e.g. top and bottom section, may also prevents the clasp from opening or deactivating when a metal item with magnetic properties is adjacent to the clasp.

When the first quick disconnecting means 18 and the second quick disconnecting means 20, comprising magnets are plated with a precious metal or noble metal or some other non magnetic metal, the magnetic flux emanating from the clasp may be about 5.2 Gauss measured at about a one inch distance. This measured magnetic flux may be well below 90 Gauss, which is the generally accepted level of magnetic flux that can interfere with the safe operation of a pacemaker, implanted cardiac defibulator or other implantable medical device. Note that a one inch measurement is used because most implanted medical devices are positioned with at least one inch of muscle, tissue and/or skin between the device and the surface of the skin. The low magnetic flux emanating from clasp 20 allows it to be used safely in medical environments such as clinics and hospitals.

FIG. 2 is a perspective view of clasp 20 shown in FIG. 1 in its assembled and locked configuration.

Because of the ease of magnetic attraction, the present invention can be used by disabled individuals unable to fasten more conventional clasps. Polarity will align the respective surfaces of the magnets and the interlocking surfaces 28, 30 will align and mate to close the clasp.

Referring back to FIG. 1, in an exemplary configuration of the present invention, clasp 10 measures from about 2 inches to about 4 inches in length, such that when it is folded over to encircle a nasal tube and attach to a person's clothing, it will have about half such extension, e.g. when the magnets are attached to each other, the length of the clasp is halved.

Attached at the one end of the clasp is preferably at least one magnet, more preferably two and even more preferably three or more magnets—as the strength of the magnet is such that with multiple magnets one can more easily reversibly detach the clasp ends form each other, e.g. with a single very strong magnet, while attractant ends may securely secure a tube to a person's clothing in a desired manner, there may be difficulty by some in achieving dissociation of the clasp with such a single strong magnet. With more than one, preferably two or more magnets employed on at least one end, the dissociation with the other end is facilitated.

In some embodiments of the present invention, the first quick disconnecting means 18 and the second quick disconnecting means 20, comprising magnets are attracted by the magnetic north-south orientation so that when they align, they quickly lock together.

In one embodiment there is an annular ring that encompasses the nasal tube, whether being an entire circle or a partial one, so that the nasal tube can be pressed into the annular structure via being momentarily compressed into the ring through a slit sufficient to permit passage of the compressed tube, but also being encircling enough to retain the nasal tube.

Some pacemakers, implanted cardiac defibrillators and other implanted medical equipment can be disrupted by magnetic fields of about 90 Gauss or stronger. Thus, in a preferred embodiment, the magnets employed are encapsulated or otherwise shielded to reduce magnetic flux significantly below the problematic level so the clasp can be safely used in proximity of this sensitive equipment.

Other embodiments of the invention relate to a clasp that includes a top portion and bottom portion, whether connected or not, that are adapted and configured to substantially surround at least one tube (e.g. a nasal tube descending form a person's nose region and extending downward across the chest region of a person.) While certain embodiments employ flexible materials having magnetic attachment elements, other embodiments include more rigid materials, especially those formed to accommodate the curved nature of the tubes intended to be encircled or restrained.

In an exemplary embodiment, the clasp is made of a material with non-magnetic properties such as fabric or plastic, and the ends of such fabric/plastic have magnets associated therewith, such that when the respective opposite ends of the fabric are brought into contact with each other, the fabric encircles the descending nasal tube in the area of a person's chest or other regions of a person's torso, such that the nasal tube is retrained in a fashion to reduce the risk that it will get unintentionally snagged by furniture or other obstacles a person wearing such nasal tube may encounter.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

To comply with appropriate written description and enablement requirements and to provide sufficient guidance in how one of skill in the art can make and use the various and numerous embodiments of the present invention, incorporated herein in their entireties are the following: U.S. Pat. Nos. 6,622,349, 6,367,126; 8,615,853; US2012/0118923 and U.S. Pat. No. 7,207,091.

In preferred embodiments, a nasal tube magnetic fastener is provided that has at least one magnet on one end of a length of a flexible material with a magnet associated with one end thereof and another end having either a magnet or a magnetically attractable portion, such that a user can encircle a nasal tube and associate the tube to a person's clothing, preferable in the region of a shirt or blouse overlapping fabric section, thus achieving the desired result of entraining the nasal tube to the person's upper garment in a manner that does not harm the fabric of the person's clothing, while also restraining the movement of the nasal tube. A user thus is provided with a way to control the position of the tube in a way that is particularly useful in circumstances in which the fasteners are required to be done and undone with a single hand and within a short time. For example, magnetic fasteners are useful in costumes for artists or performers who need to change frequently on stage. They are also useful for workers who wear work clothes and vests which may be caught by machinery or moving objects. Clothes or work vests with magnetic buttons provide easy escape to save the wearer from being caught and hurt when the clothes or vests are engaged accidentally.

As mentioned above, typical magnetic buttons include a pair of complementary parts which are releasably attachable to each other by magnetic attraction. Each of the detachable parts usually includes a magnetic member in slab or tablet form having a top and a bottom magnetic coupling surfaces with the opposite magnetic poles formed on them. The magnetic coupling surfaces are usually interconnected by a continuous peripheral edge which is usually quite thin for aesthetic and styling consideration. The magnetic slabs or tablets are usually cylindrical in shape with substantially identical top and bottom surfaces.

The magnetic enclosures that can be employed include magnetic permeable materials which are made, for example, of rubber, Nylon, fabrics, plastics (such as ABS or PVC) or synthetic resin. Any decoration to the magnetic fasteners can be selected to provide an aesthetic design to the magnetic clasping member. While the material entrapping the magnetic ends is preferably washable, it can alternatively be made form a material (metal, plastic, etc.) that is water resistant so that even if the magnet member is oxidized, the enclosure still provides a cosmetic cover thereto. In certain embodiments, the material extending between the magnetic sections of the clasp are transparent so as to be less noticeable when worn. Other embodiments can include glow in the dark materials used in making the clasps as to assist those users to locate the clasp when in the dark or dim light conditions.

To further enhance the convenience and usefulness of magnetic clasps of the present invention, magnetic fasteners are preferably made with complementary magnetic members having identical shapes and dimensions. As a result of the substantially identical dimensions of the complementary magnetic coupling surfaces on the detachable parts, the parts will come into substantially automatic alignment once they come into contact and no external help is therefore required in general for the initial contact and the subsequent engagement.

The present invention in many embodiments provides for a lightweight, reliable and simple strap fastener for a nasal tube that can be connected to a person's clothing in a prompt and repeatable fashion, that is easily disengageable as and when desired by the user.

Throughout this specification, the terms fasteners, buckles and buttons are used interchangeably for brevity and succinctness to the extent that is appropriate for the context.

Preferably the clasp for a nasal tube is have a low-profile build so that it can be easily and conveniently used in association with upper torso garments, such as shirts or blouses or pajamas or robes, and that retrains the movement of the a nasal tube, once encircled, to connect the tube in a fashion such that it is operatively connected to the person's clothes for aesthetic consideration.

In other embodiments, the clasp can be of a two piece design, such that a magnet is employed on one surface of a person's clothing, with the opposite surface of the clothing having another magnet or a magnetically attracted metal portion or segment provided such that upon the association of the magnet to such other portion, a nasal tube is entrained so as to be associated with the person's clothing, such as to avoid tripping over or entanglement with the nasal tube.

In certain embodiments, the clasp member includes a holder for receiving a magnetic member so that at least one surface of said magnetic member is magnetically coupled with a counter-part strap fastener of the same design, said elevated portion will not push against the strap receiving means of the counter-part fastener while forming a barrier member to stop relative lateral movement along the directions of the strap receiving means.

According to yet another aspect of the present invention, there is provided a clasp for a nasal tube comprising a pair of engageable magnetic fasteners of opposite polarity to each other engageable or a common axis and a strap engagement portion connected to each magnetic fastener and extending transverse to said common axis of engagement of said magnetic fasteners. Preferably, said fastener includes at least one protrusion to reside against a perimeter of an opposed magnetic fastener to resist movement of one magnetic fastener with respect to the other transverse to said common axis on which they engage.

A further aspect of the present invention, is a nasal tube clasp comprising a loop comprising a first end, a second end, a length spanning between the first end and the second end, and a width, and at least one quick-disconnecting means, wherein each quick disconnecting means further comprises a first piece attached to the first end of the loop, and a second piece attached to the second end of the loop, wherein the first piece and second piece can be reversibly attached to each other to form an annular space surrounded by the loop, wherein the nasal tube is secured within the annular space when the first piece and second piece are attached, and wherein the nasal tube is released from the annular space when the first piece and second piece are detached.

In some embodiments of the present invention, a nasal tube fastener or clasp comprising a quick-disconnecting means and a loop are sufficient to restrain a tube within an annular space formed by the loop and form a releasable attachment to the user. The embodiments shown in FIGS. 1 and 2 illustrate such a design. In these embodiments, the clasp 10 comprising a first piece 18 and a second piece 20 of a quick-disconnecting means, for example comprising magnets, form an attachment to the user's garment by sandwiching the garment between the two opposing magnets within the annular space 26 formed by the loop 22 when the magnets are in contact.

Referring to FIGS. 3A and 3B, in further embodiments of the present invention, the clasp 10 further comprises an attachment means 24, wherein the attachment means 24 provides a removable attachment to the users garment. Referring to FIG. 3B, in some embodiments, the attachment means 24 may comprise a swatch or patch of fabric with a hole 32 therethrough, such that a button on a users shirt, pajama top, etc. can be place through the hole 32 in the attachment means 24, thereby securing it to the garment. In this embodiment, the tubing is then placed between the two opposing arms of the loop 22 and the first and second pieces of the quick-disconnecting means are reversible connected to secure the tubing in the annular space formed. The two opposing arms may be separate and distinct, whereby each is separately attached to the attachment means 24, or the two opposing arms may be a single continuous piece of material.

In some embodiments of the present invention, the attachment means 24 may comprise a pin and pin-receiver, wherein the pin punctures a hole through the user's garment (e.g. a T-shirt) and the pin-receiver receives the pin to hold the attachment means 24 in place, and wherein the pin-receive protects the wearer from being injured by the pin. Alternatively, a pin can be placed on the inside surface of a garment, whereby after the pin punctures the fabric, the pin is exposed on the outside surface of the garment, such that the pin-receiver receives the pin outside the garment, holds the clasp in place against the garment and provides a mechanical cover for protecting the wearer from the pin by covering the pin.

In some embodiments of the present invention, the opposing faces of the first piece and second piece of quick-disconnecting means may comprise a first interlocking surface and a second interlocking surface that are substantially perpendicular to the longitudinal axis of the loop. In further embodiments of the present invention, the opposing faces of the first piece and second piece of quick-disconnecting means may comprise a first interlocking surface and a second interlocking surface that are substantially parallel to the longitudinal axis of the loop. Referring to FIG. 3B, the opposing faces of the first piece 18 and second piece 20 of quick-disconnecting means may comprise a first interlocking surface 28 and a second interlocking surface 30 that are substantially parallel to the longitudinal axis of the loop 22. It is perceived by the inventor, that the differing orientation of the surfaces relative to the longitudinal axis of the loop will further allow one to fine tune the forces needed to separate the two opposing surfaces. These surfaces may simply be magnetic surfaces, or Velcro™, mechanical snaps, and combinations thereof. For example a magnetic surface may further comprise a mechanical snap situated on the surface.

Referring now to FIG. 4, another embodiment of the present invention is illustrated, a tube retaining device 34 comprises passing the oxygen tube 16 through a tube 36. In such an embodiment, the retaining device 34 may comprise more than clasp 10 attached to the tube; e.g. a first clap to be attached at the neck of a garment, a second clasp for attaching to a midsection of a garment, and a third clasp for attaching to the waist-section of a garment. In some embodiments of the present invention, the retaining device 34 may comprise a length from about 10 cm to about 100 cm. In some embodiments, the tubing retaining device may comprise from 1 to 10 clasps. In some further embodiments, the tubing retaining device may comprise from 2 to 5 clasps.

In some embodiments of the present invention, the loop may comprise a length ranging from about 2 cm to about 10 cm. In some embodiments the loop may comprise a length of about 2 cm, 3 cm, 4 cm, 5 cm, 6 cm, 7 cm, 8 cm, 9 cm, or about 10 cm. In some embodiments of the present invention, the loop may comprise a material of construction comprising at least one of fabric, plastic, metal and combinations thereof. In some embodiments of the present invention, the loop may comprise a flexible planar structure comprising a first end a second end and a length spanning between the first end and the second end. In some embodiments of the present invention, the loop may comprise a laminated flexible planar structure comprising an inner layer facing the annular space, and an outer layer facing away from the annular space; e.g. towards the outside, or towards the patient's environment. In some embodiments, a loop comprising a laminated flexible planar structure may comprise an inner layer constructed of a fabric which resists movement by the tube inside the annular space. This feature provides the added operational benefit of maintaining the longitudinal position of the tube within the clasp. The user can place the length of the tube to a desired position, after which the tube will be more likely to remain in that position (e.g. despite movement in bed, or walking, eating, etc.) due to the resistance to movement provided by the inner layer. In some embodiments, the outer layer of the loop may comprise a fabric, and the inner layer may comprise a plastic material. Since typical medical tubing for supplying oxygen comprises a plastic material (e.g. Tygon® tubing), an inner layer comprising plastic will provide more resistance to movement than an inner layer comprising a fabric material.

Referring again to FIG. 3A, the loop 22 may also be in the form of a rope, string, lace, or thin section of fabric, wherein the first piece of the first quick-disconnecting means 18 and the second piece of the quick-disconnecting means 20 are physically attached to the first end and second end respectively of the loop. However, referring to FIG. 2, further embodiments of the present invention, may place, secure, fasten, and sew the first piece of the quick-disconnecting means 18 and the second piece of the quick-disconnecting means 20 to or within the loop 22 itself.

In some embodiments of the present invention, the first piece of the quick-disconnecting means 18 and the second piece of the quick-disconnecting means 20 may comprise magnets, Velcro™, snaps, clasps, and any other suitable quick-disconnecting devices that can be reversibly attached and will separate when a maximum force is applied to either the quick-disconnecting means, or the tube being held by the quick-disconnecting means. In some embodiments of the present invention, the first piece of the quick-disconnecting means 18 and the second piece of the quick-disconnecting means 20 may be designed to separate when a maximum force of 0.1 newton (1 kg*m/s$^2$) is applied. In still further embodiments of the present invention, the first piece of the quick-disconnecting means 18 and the second piece of the second quick-disconnecting means 20 may be designed to separate when a maximum force of 0.01 newton, 0.1 newton, 1.0 newton, 10 newton, 100 newton, or 1000 newton is applied.

Figure 5:
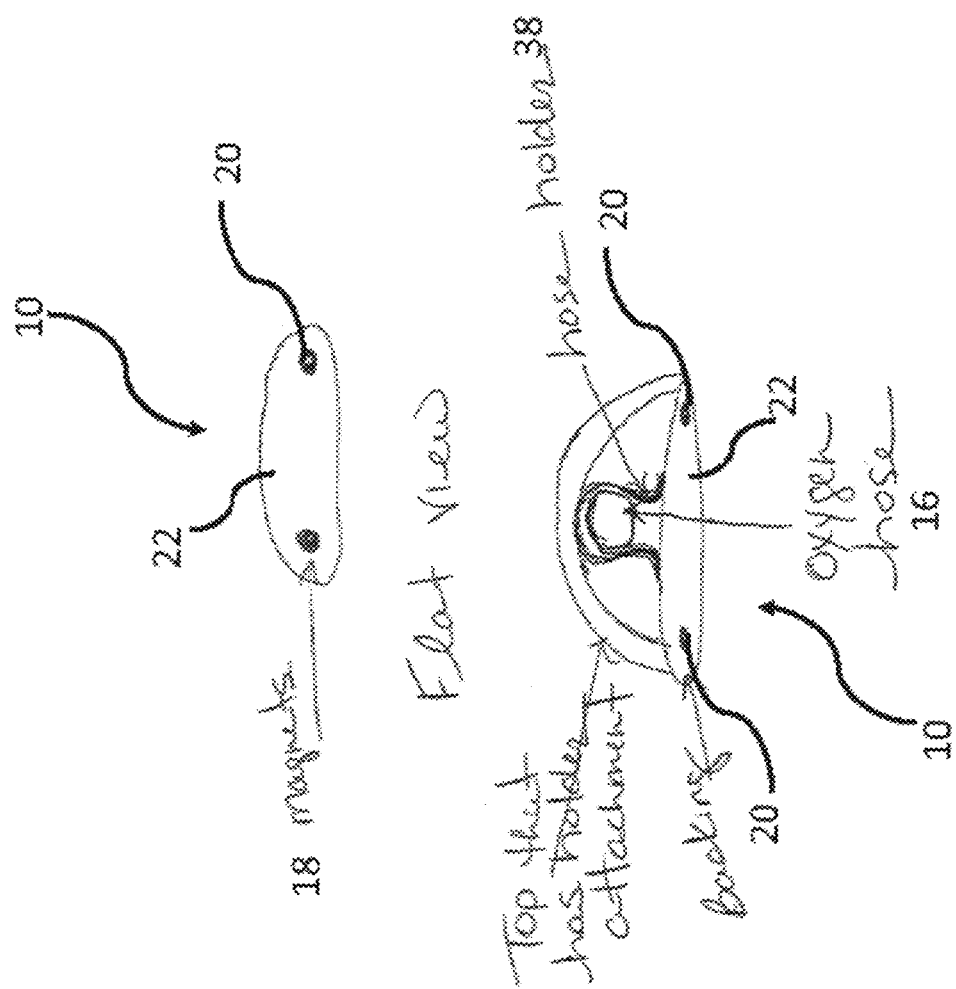
FIG. 5 illustrates a perspective view of a clasp assembly of the present invention.

Referring now to FIG. 5, in some embodiments of the present invention, a clasp 10 may comprise a loop 22 to which is attached a holder 38 which is adapted to secure the oxygen tubing or hose to the clasp. In such an embodiment, the first piece 18 and second piece 20 of the quick-disconnecting means mate against one another to form a reversible connection, much like described above for FIGS. 1 and 2. However, in this case, the annular space created by this connection is not used to secure the tubing. Instead, the holder 38 secures the tubing. The holder 38 may comprise a ring through which the tubing is threaded. Alternatively, the holder 38 may comprise a C-shaped receiver into which the tubing can be positioned; e.g. with a "snap-in" functionality.

Figure 6:
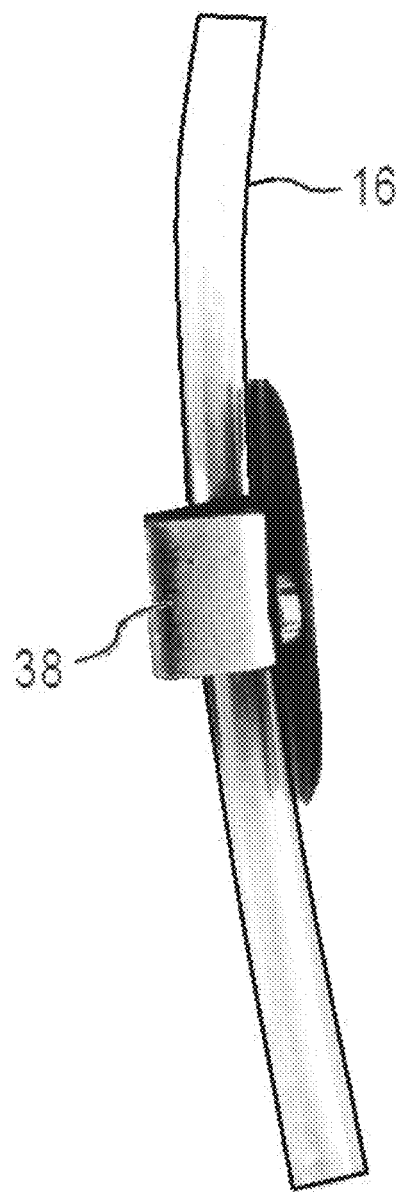
FIG. 6 illustrates a side view of a clasp assembly of the present invention.

Referring now to FIG. 6, a hose 16 may be secured to a backing portion via a holder 38. The hose 16 may be clear plastic as shown in FIG. 6, or in alternative embodiments, the hose 16 may be braided steel, glow-in-the dark, opaque plastic, or any other tubular structure used to transport gas.

The holder 38 constrains the movement of the hose 16 in at least two directions. In some embodiments, the hose 16 may be allowed to slide through the holder 38 while being restrained in two directions. In various embodiments, the hose 16 may not slide relative to the holder 38, and the hose 16 is in a fixed position relative to the holder 38.

The holder 38 is connected to a backer as shown in FIG. 6. This connection may be a fixed connection, a rotatable connection, a magnetic connection, etc. The backer is a two-part component in some embodiments, and the two pieces are connected magnetically. This allows a user to connect a hose 16 on one portion of the backer (e.g., via positioning the hose between the spring arms of a reversible hose holder mechanism) and locate the other portion of the backer behind an article of clothing or other object. Then the two portions are magnetically coupled, and the hose 16 is positioned on a particular location of the user's clothing or other object.

Figure 7:
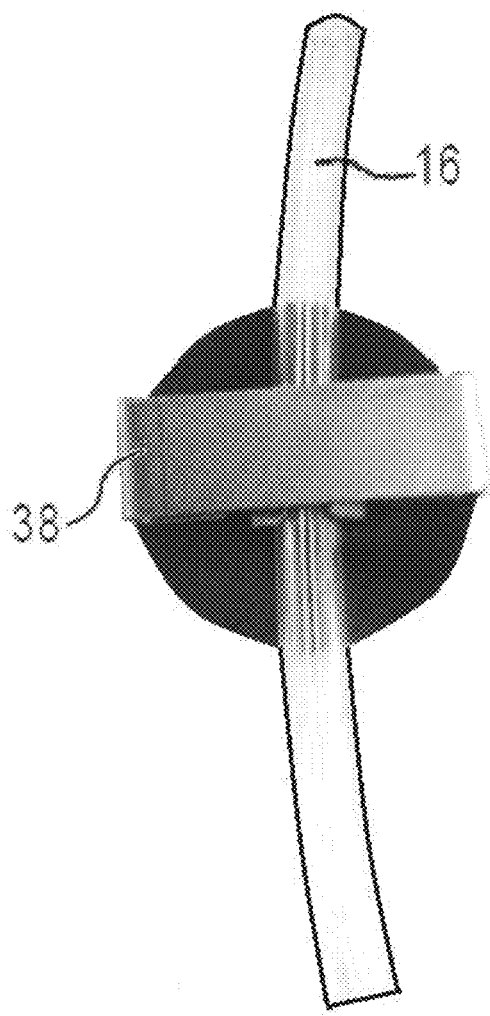
FIG. 7 illustrates a front view of a clasp assembly of the present invention.

Referring now to FIG. 7, a front view of the hose 16, holder 38, and backer combination is shown. The holder 38 may fully encircle the hose 16 in some embodiments. In various embodiments, the holder 38 partially encircles or encloses the hose 16 such that the hose 16 may snap or be selectively interconnected to the holder 38, e.g., prior to the holder (now with an associated hose attached thereto) being magnetically affixed to clothing.

Figure 8:
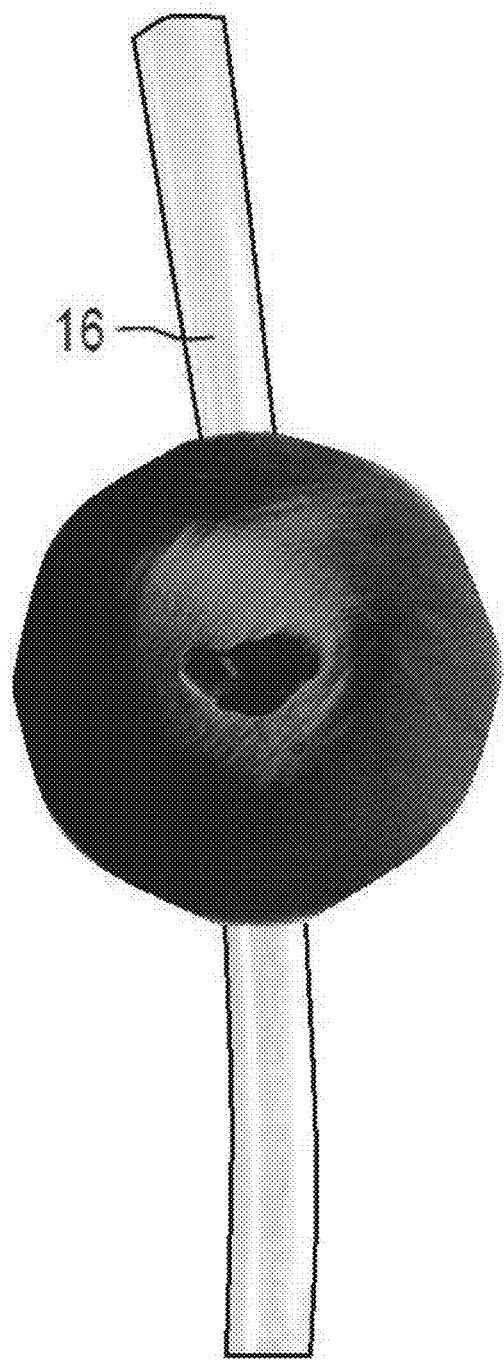
FIG. 8 illustrates a rear view of a clasp assembly of the present invention.

Referring now to FIG. 8, a rear view of the backer is shown. In some embodiments, the two backer portions are magnetically coupled. In other embodiments, the backer is a single portion that comprises a safety pin-like protrusion such that the backer penetrates an article of clothing or other object.

Further, the backer may be shaped like a tie clip such that the backer clamps to an edge of an article of clothing or other object.

Figure 9A:
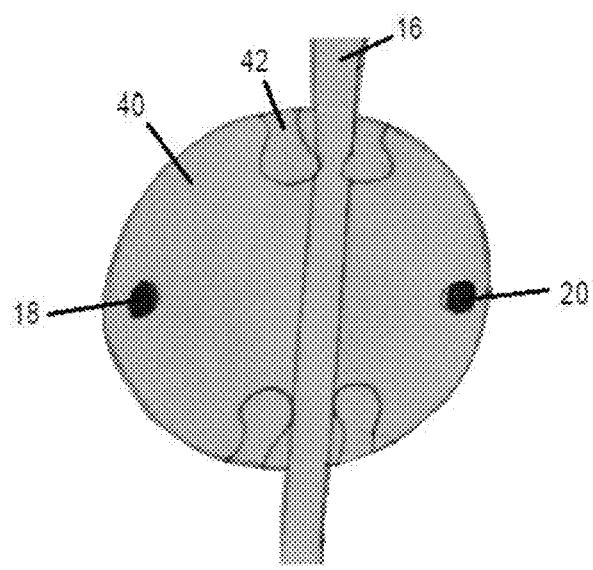
FIG. 9A illustrates a front view of a backing portion of the present invention.
Figure 9B:
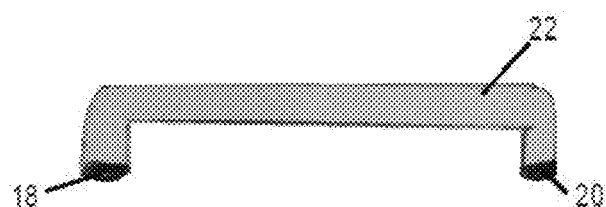
FIG. 9B illustrates a front view of a bar of the present invention.
Figure 9C:
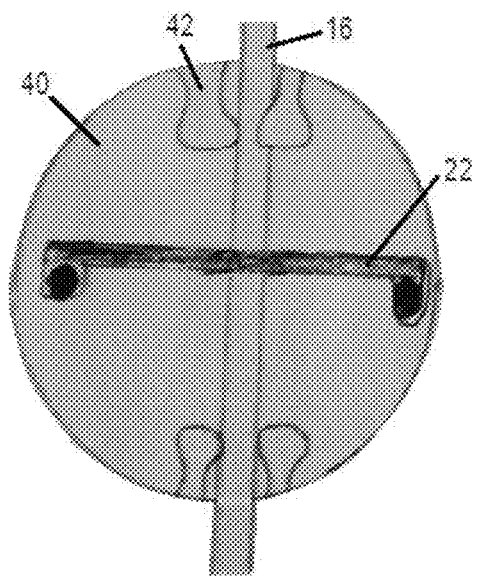
FIG. 9C illustrates a front view of a backing portion and bar assembly of the present invention.

Referring now to FIGS. 9A to 9C, an embodiment of a backing portion 40 and loop or bar 22 is provided. A backing portion 40 comprising a first and second magnet 18, 20 is shown in FIG. 9A. The backing portion 40 has a generally circular shape, but one skilled in the art will appreciate alternative shapes such as rectangular, ovoid, triangular, polygonal, amorphous, fractal, etc. The magnets are generally disposed along a lateral axis of the backing portion 40.

The backing portion 40 in FIG. 9A has four prongs 42 situated along a longitudinal axis of the backing portion 40. In embodiments where the backing portion 40 is stamped from stock material, the prongs 42 may be included in the stamping process, and then folded around to the side of the backing portion 40 shown in FIG. 9A. A hose 16 may be oriented along the longitudinal axis of the backing portion 40, and the prongs 42 may be folded over to secure the hose 16 to the backing portion 40. In this embodiment, each prong 42 comprises two ends that protrude in opposing directions. These ends allow at least a portion of the prong 42 to be disposed over the hose 16 in order to secure the hose 16 to the backing portion 40. There are two sets of two prongs 42 shown in FIG. 9A. One set of prongs 42 is disposed on the top end of the backing portion 40, and one set of prongs 42 is disposed on the bottom end of the backing portion 40. Alternative embodiments may only have one set of prongs 42 disposed anywhere between the top and bottom ends of the backing portion 40. Other alternative embodiments may have odd numbers of prongs 42, prongs 42 without sets, etc.

FIG. 9B shows a loop or bar 22 that has two ends. First and second magnets 18, 20 are disposed at the first and second ends of the bar 22, respectively. As shown in FIG. 9C, this bar is positioned over the backing portion 40 and the hose 16 and magnetically secured to the backing portion 40. The backing portion's 40 first magnet 18 and the bar's 22 first magnet 18 are dipolar and are oriented such that the backing portion 40 and the bar 22 are attracted to each other in close proximity. Similarly, the backing portion's 40 second magnet 20 and the bar's 22 second magnet 20 are dipolar and are oriented such that the backing portion 40 and the bar 22 are attracted to each other in close proximity. Once the bar 22 and the backing portion 40 are magnetically secured to each other, the bar 22 secures the hose 16 along with the prongs 42. Embodiments of the invention shown in FIGS. 9A to 9C may optionally include the prongs 42 or optionally include the bar 22.

While the present invention has been explained by reference to the preferred embodiments above, it should be appreciated that the embodiments are provided for illustration and assisting understanding only and do not intend to limit or restrict the scope of the present invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

What is claimed is:

1. A nasal tube fastener system, comprising:
a nasal tube adapted to be secured to a person's nostrils;
a first fastener having a strap with a first end and a second end;
wherein a first magnetic member is positioned at the first end of the strap, and a second magnetic member is positioned at the second end of the strap;
wherein the strap extends at least two inches between the magnetic members;
wherein the first magnetic member has a first magnetic surface of a first magnetic polarity, and the second magnetic member has a second magnetic surface of a second, opposite magnetic polarity; and
wherein the strap is conformed around the nasal tube, with the first magnetic surface being positioned on one side of a fabric, and the second magnetic surface being positioned on the opposite side of the fabric.

* * * * *